United States Patent
Lee et al.

(10) Patent No.: US 7,935,474 B2
(45) Date of Patent: May 3, 2011

(54) ACID-AMPLIFIER HAVING ACETAL GROUP AND PHOTORESIST COMPOSITION INCLUDING THE SAME

(75) Inventors: Jung-Youl Lee, Anyang-Si (KR); Min-Ja Yoo, Boryeong-si (KR); Jeong-Sik Kim, Hwaseong-Si (KR); Young-Bae Lim, Hwaseong-Si (KR); Jae-Woo Lee, Bucheon-Si (KR); Jae-Hyun Kim, Seoul (KR)

(73) Assignee: Dongjin Semichem Co., Ltd., Incheon (KR)

( * ) Notice: Subject to any disclaimer, the term of this patent is extended or adjusted under 35 U.S.C. 154(b) by 390 days.

(21) Appl. No.: 12/174,759

(22) Filed: Jul. 17, 2008

(65) Prior Publication Data
US 2009/0023093 A1  Jan. 22, 2009

(30) Foreign Application Priority Data
Jul. 20, 2007 (KR) .................. 10-2007-0073117

(51) Int. Cl.
G03F 7/004 (2006.01)
G03F 7/30 (2006.01)

(52) U.S. Cl. .............. 430/270.1; 430/326; 430/330; 430/922; 549/32

(58) Field of Classification Search .......... 430/270.1, 430/326, 330, 922; 549/32
See application file for complete search history.

(56) References Cited

U.S. PATENT DOCUMENTS
4,466,977 A   8/1984 McMillan et al.
6,894,084 B2 * 5/2005 Kovar et al. ............... 522/150

FOREIGN PATENT DOCUMENTS
EP  1 780 198        5/2007
JP  11 158118 A      6/1999
JP  2005 342913 A   12/2005

OTHER PUBLICATIONS

David A. Clark et al., Cytochalasin Support Studies. Macrocycle Synthesis via Enolate-Assisted, Intraannular, 1,4-Fragmentation Reactions, 101:13, Jun. 20, 1979, American Chemical Society.

* cited by examiner

Primary Examiner — John S Chu
(74) Attorney, Agent, or Firm — Birch, Stewart, Kolasch & Birch, LLP

(57) ABSTRACT

An acid-amplifier having an acetal group and a photoresist composition including the same, are disclosed. The acid-amplifier produces an acid (second acid) during a post-exposure-bake (PEB), which is induced by an acid (first acid) generated from a photo-acid generator (PAG) at the exposure process so that a line edge roughness (LER) of the photoresist pattern and photoresist energy sensitivity are improved. The acid-amplifier has a structure of following Formula 1.

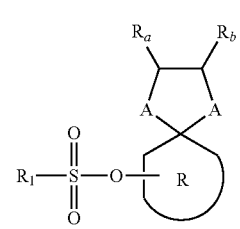

[Formula 1]

in Formula 1, R is $C_4$~$C_{20}$ mono-cyclic or multi-cyclic saturated hydrocarbon, $R_1$ is $C_1$~$C_{10}$ linear hydrocarbon, $C_1$~$C_{10}$ perfluoro compound or $C_5$~$C_{20}$ aromatic compound, $R_a$ and $R_b$ are independently hydrogen atom or $C_1$~$C_4$ saturated hydrocarbon and A is independently oxygen atom (O) or sulfur atom (S).

6 Claims, 1 Drawing Sheet

[FIG. 1]
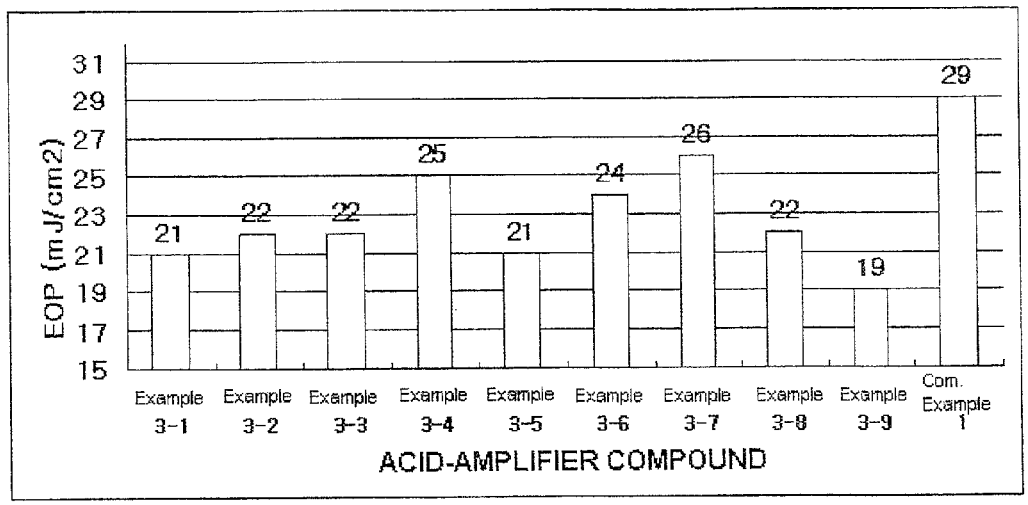
[FIG. 2]
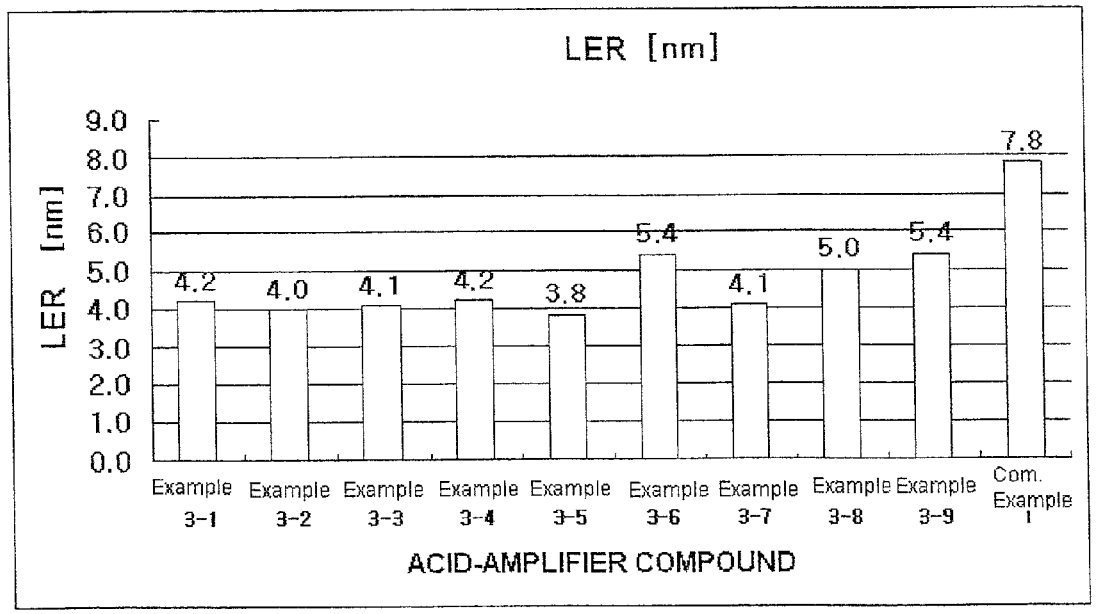

ACID-AMPLIFIER HAVING ACETAL GROUP AND PHOTORESIST COMPOSITION INCLUDING THE SAME

This application claims the priority benefit of Korean Patent Application No. 10-2007-0073117 filed on Jul. 20, 2007. All disclosure of the-Korean Patent application is incorporated herein by reference.

FIELD OF THE INVENTION

This invention relates to an acid-amplifier and a photoresist composition including the same, and more specifically to an acid-amplifier having an acetal group and a photoresist composition including the same. The acid-amplifier contained in the photoresist composition according to the present invention produces an acid (second acid) during a post-exposure-bake (PEB), which is induced by an acid (first acid) generated from a photo-acid generator (PAG) at the exposure process. Therefore a line edge roughness (LER) of the photoresist pattern and photoresist energy sensitivity could be improved.

BACKGROUNDS OF THE INVENTION

The photolithography is a process used to form a circuit pattern of a semiconductor chip or a display element from a semiconductor wafer or a glass for the display element. The photoresist composition is the most essential materials to the photolithography process. So, recently, as the patterns for semiconductor devices and the display elements are finer, the need for the photoresist composition having high resolution is more increased.

Conventional acid-amplified photoresist composition includes a polymer resin, a PAG, an organic solvent and if needed, a base compound. Since the conventional photoresist composition includes the polymer resin as a main component, it has excellent mechanical properties such as processibility, coating stability and etching resistance and can be easily removed after the succeeding process including an etching process, an ion implantation process etc. In the photoresist composition, the PAG having good energy sensitivity to an exposure light enables the fine pattern of the photoresist. However, with only the conventional PAG, the photoresist energy sensitivity cannot be sufficiently increased. Accordingly, the LER of the photoresist pattern formed is still not satisfactory.

SUMMARY OF THE INVENTION

Therefore, it is an object of the present invention to provide an acid-amplifier which improves the LER of a photoresist pattern and photoresist energy sensitivity, and a photoresist composition including the same.

It is another object of the present invention to provide an acid-amplifier which improves a focus margin of process and is useful for a formation of fine photoresist pattern, and a photoresist composition including the same.

To accomplish these objects, the present invention provides an acid-amplifier having a structure of Formula 1 and generating a second acid from an acid which is produced from a PAG by an exposure to light.

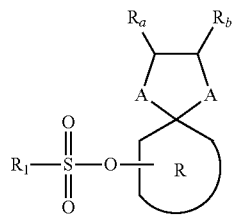

[Formula 1]

In Formula 1, R is $C_4$~$C_{20}$ mono-cyclic or multi-cyclic saturated hydrocarbon, $R_1$ is $C_1$~$C_{10}$ linear hydrocarbon, $C_1$~$C_{10}$ perfluoro compound, or $C_5$~$C_{20}$ aromatic compound. $R_a$ and $R_b$ are independently hydrogen atom or $C_1$~$C_4$ saturated hydrocarbon and A is independently oxygen atom (O) or sulfur atom (S).

The present invention also provides a photoresist composition comprising 0.01~5 weight % of an acid-amplifier having a structure of the above Formula 1, 3~10 weight % of photo-sensitive polymer, 0.05~10 weight part of a PAG with respect to 100 weight part of the photo-sensitive polymer and a remaining organic solvent.

BRIEF DESCRIPTION OF THE DRAWINGS

FIG. 1 shows a bar graph illustrating EOP (mJ/cm$^2$) of the photoresist patterns formed by using photoresist compositions obtained from Examples and a Comparative Example of the present invention.

FIG. 2 is a bar graph illustrating LER of the photoresist patterns formed by using photoresist compositions obtained from Examples and a Comparative Example of the present invention.

DETAILED DESCRIPTION OF THE INVENTION

A more complete appreciation of the invention, and many of the attendant advantages thereof, will be better appreciated by reference to the following detailed description.

The new acid-amplifier according to the present invention, as a compound capable of producing a second acid which is induced from an acid generated at an exposure to light, contains acetal or thioacetal structure in the molecule thereof. In detail, the new acid-amplifier has a structure of following Formula 1.

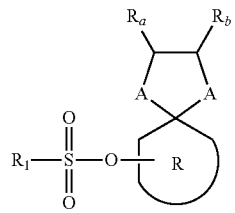

[Formula 1]

In Formula 1, R is $C_4$~$C_{20}$ mono-cyclic or multi-cyclic saturated hydrocarbon, $R_1$ is $C_1$~$C_{10}$ linear hydrocarbon, $C_1$~$C_{10}$ perfluoro compound, or $C_5$~$C_{20}$ aromatic compound. $R_a$ and $R_b$ are independently hydrogen atom or $C_1$~$C_4$ saturated hydrocarbon and A is independently oxygen atom (O) or sulfur atom (S). The examples of the linear hydrocarbon used as $R_1$ includes methyl group, ethyl group, propyl group, isopropyl group, tert-butyl group, n-butyl group and hexyl group, etc. The examples of perfluoro compound used as $R_1$ includes perfluoromethyl group, perfluoroethyl group, perfluoropropyl group, perfluorobutyl group and perfluorohexyl group, etc. The examples of aromatic compound used as $R_1$ includes benzene group, toluene group and tert-butyl benzene group, etc. Also, R, $R_1$, $R_a$ and $R_b$ may be substituted with $C_1$~$C_4$ alkyl group or halogen atom or may not be substituted.

The representative examples of the acid-amplifier represented by Formula 1 are as follows.

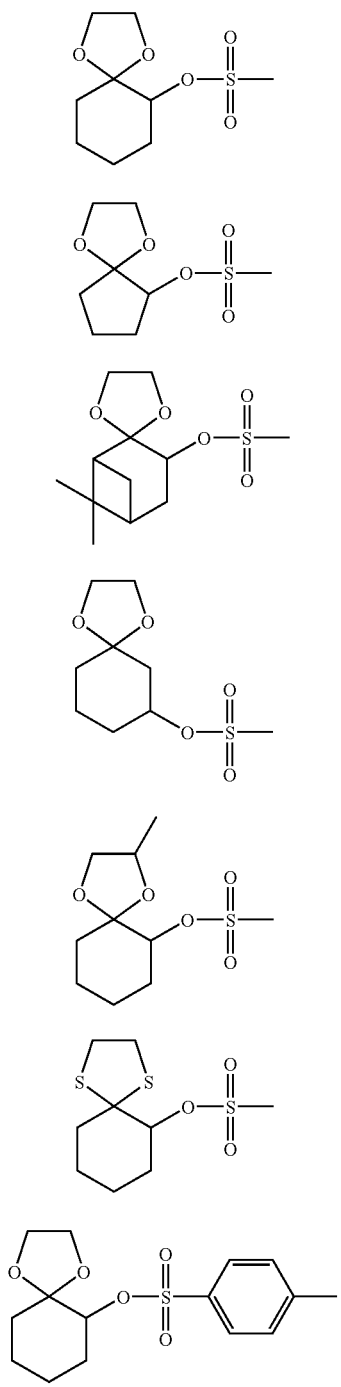

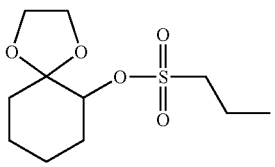

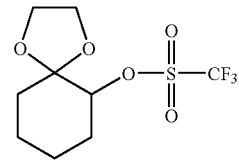

For manufacturing the acid-amplifier of Formula 1, firstly, an intermediate represented by Formula 4 is prepared by reacting hydroxy ketone compound of Formula 2 with a compound of Formula 3 having two alcohol groups or thio alcohol groups, as shown in following Reaction 1.

[Reaction 1]

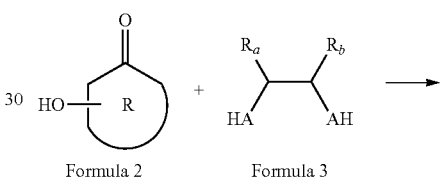

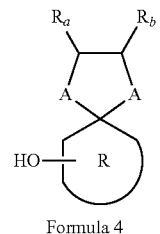

In Reaction 1, R, $R_a$, $R_b$ and A are the same as defined in Formula 1. The reaction of Reaction 1 is carried out at room temperature and atmospheric pressure. The reaction product is washed with water several times to remove a by-product and then re-crystallized with acetone so that intermediate of Formula 4 is prepared.

The examples of hydroxy ketone compound represented Formula 2 include

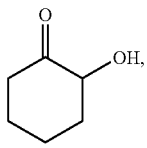

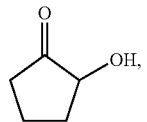

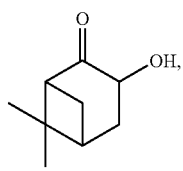
(Formula 2c)

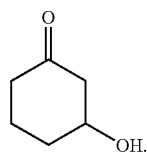
(Formula 2d)

The examples of compound represented by Formula 3 include

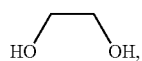
(Formula 3a)

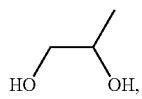
(Formula 3b)

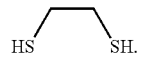
(Formula 3c)

The examples of intermediates represented by Formula 4 include

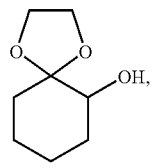
(Formula 4a)

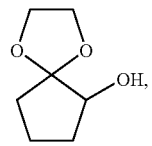
(Formula 4b)

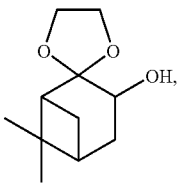
(Formula 4c)

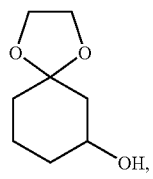
(Formula 4d)

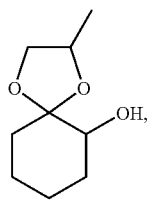
(Formula 4e)

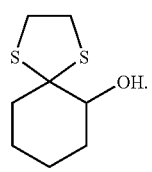
(Formula 4f)

Next, as shown in following Reaction 2, the intermediate represented by Formula 4 sulfonyl halide represented by Formula 5 are reacted to prepare the acid-amplifier of Formula 1. The reaction of Reaction 2 is carried out at room temperature and atmospheric pressure. The reaction product is washed with water several times to remove a by-product and then re-crystallized with hexane, etc so that the acid-amplifier of Formula 1 is prepared.

[Reaction 2]

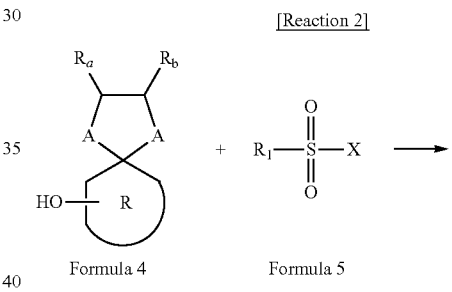

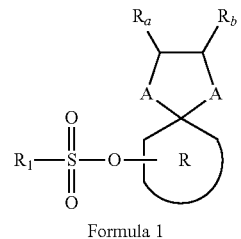

Formula 1

In Reaction 2, R, $R_1$, $R_a$, $R_b$ are the same as defined in Formula 1, X represents halogen atom or bromine atom, and sulfonyl halide represented by Formula 5 includes

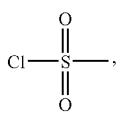
(Formula 5a)

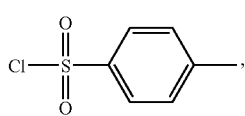
(Formula 5b)

-continued

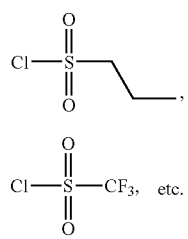

(Formula 5c)

(Formula 5d)

The acid-amplifier according to the present invention generates an acid (second acid) during a post-exposure-bake (PEB), which is induced by an acid (first acid) generated from a photo-acid generator (PAG) at the exposure process. Therefore the LER of the photoresist pattern and photoresist energy sensitivity are improved.

A photoresist composition according to the present invention includes the acid-amplifier represented by Formula 1, a photo-sensitive polymer, a PAG and an organic solvent. And if needed, the photoresist composition further includes a base compound as a quencher and a surfactant. An amount of the acid-amplifier represented by Formula 1 is 0.01~5 weight %, preferably 0.5~2 weight % and an amount of the photo-sensitive polymer is 3~10 weight %, preferably 3~5 weight %. Preferable amount of the PAG is 0.05~10 weight part with respect to 100 weight part of the photo-sensitive polymer and the rest component of the photoresist composition is the organic solvent. If the base compound is used, the amount thereof is 0.01~10 weight %, preferably 0.01~2 weight %, with respect to the total photoresist composition.

If the amount of the acid-amplifier is too little, amount of second acid generated is little so that the improvement of the LER is slight. If the amount of the acid-amplifier is too much, excess amount of the second acid is generated to let pattern profile uneven and adhesive strength against the contact be weakened. Therefore, the pattern cannot be easily formed. If the amount of the photo-sensitive polymer is too little, it is difficult to form the resist film with a desired thickness. If the amount of the photo-sensitive polymer is too much, thickness of patterns on the wafer is not uniform. Also, if the amount of the base compound is too little, it is not easy to control a diffusion of the acid generated in an exposure process so that the pattern profile is uneven. If the amount of the base compound is too much, the diffusion of the acid generated is suppressed so that pattern is not easily formed. Further, If the amount of the PAG is too little, the light sensitivity of the photoresist composition may decrease. If the amount of the PAG is too much, the profile of the resist patterns may be deteriorated because the PAG absorbs a lot of ultraviolet rays and a large quantity of acid is produced from the PAG.

As the photo-sensitive polymer, any conventional photo-sensitive polymer for the photoresist, which reacts with an acid to vary solubility to a developer, can be used. The photo-sensitive polymer, which has a protecting group sensitive to an acid and then is separated by the acid, can be preferably used. The photo-sensitive polymer may be block copolymer or random copolymer, and the weight-average molecular weight (Mw) of the photo-sensitive polymer is preferably 3,000~20,000. As the PAG, any conventional PAG, which can generate an acid when exposed to light, can be used. The non-limiting examples of the PAG include onium salts, for example sulfonium salts or iodonium salts. Specifically, the PAG is selected from a group consisting of phthalimidotrifluoromethane sulfonate, dinitrobenzyltosylate, n-decyl disulfone and naphthylimido trifluoromethane sulfonate. Also, the PAG is selected from the group consisting of diphenyl iodonium triflate, diphenyl iodonium nonaflate, diphenyl iodonium hexafluorophosphate, diphenyl iodonium hexafluoroarsenate, diphenyl iodonium hexafluoroantimonate, diphenyl p-methoxyphenyl sulfonium triflate, diphenyl p-toluenyl sulfonium triflate, diphenyl p-tert-butylphenyl sulfonium triflate, diphenyl p-isobutylphenyl sulfonium triflate, triphenylsulfonium triflate, tris(p-tert-butylphenyl) sulfonium triflate, diphenyl p-methoxyphenyl sulfonium nonaflate, diphenyl p-toluenyl sulfonium nonaflate, diphenyl p-tert-butylphenyl sulfonium nonaflate, diphenyl p-isobutylphenyl sulfonium nonaflate, triphenylsulfonium nonaflate, tris(p-tert-butylphenyl) sulfonium nonaflate, triphenylsulfonium hexafluoroarsenate, triphenylsulfonium hexafluoroantimonate, triphenylsulfonium triflate and dibutylnaphthylsulfonium triflate.

The conventional various organic solvents for the photoresist composition can be used as the organic solvent of the photoresist composition of the present invention. Exemplary organic solvent include, but are not limited to, ethyleneglycol monomethylethyl, ethyleneglycol monoethylether, ethyleneglycol monomethylether, ethyleneglycol monoacetate, diethyleneglycol, diethyleneglycol monoethylether, propyleneglycol monomethyletheracetate (PGMEA), propyleneglycol, propyleneglycol, monoacetate, toluene, xylene, methylethylketone, methyl isoamyl ketone, cyclohexanone, dioxane, methyl lactate, ethyl lactate, methyl pyruvate, ethyl pyruvate, methyl methoxy propionate, ethyl ethoxy propionate, N,N-dimethylformamide, N,N-dimethylacetamide, N-methyl 2-pyrrolidone, 3-ethoxy ethyl propionate, 2-heptanone, γ-butyrolactone, ethyl 2-hydroxy propionate, ethyl 2-hydroxy-2-methyl propionate, ethoxyethyl acetate, hydroxyethyl acetate, methyl 2-hydroxy-3-methylbutanoate, methyl 3-mrethoxy-2-methylpropionate, ethyl 3-ethoxy propionate, ethyl 3-methoxy-2-methyl propionate, ethyl acetate, butyl acetate, and the mixtures thereof. The base compound as the quencher includes tri-ethylamine, tri-iso-butylamine, tri-iso-octylamine, diethanolamine, tri-ethanolamine and mixture thereof.

The surfactant, at need, is added in the present photoresist composition so as to improve a mixing uniformity of the photoresist composition, coating property of the photoresist composition and developing property of the photoresist film after the exposure to light. As the surfactant, any conventional surfactant, which can be used in the photoresist composition, can be used. Examples of such surfactants include fluorine-based surfactant or fluorine-silicon-based surfactant. The amount of the surfactant is 0.001~2 weight part, preferably 0.01~1 weight part with respect to solid content 100 weight part of the photoresist composition. If the amount of the surfactant is too little, function of the surfactant does not sufficiently work and if the amount of the surfactant is too much, the resist property such as shape stability or a storage stability of the composition except for the coating property, may be adversely affected.

In order to form a photoresist pattern with the photoresist composition according to the present invention, the following conventional photolithography process can be carried out. First, the photoresist composition is applied or coated on a substrate such as silicon wafer, an aluminum substrate, and so on, for example, with a spin coater to form a photoresist layer. The photoresist layer is exposed to a light of a predetermined pattern. After the exposure, if necessary, the photoresist pattern is thermally treated (heated), which is called as PEB (Post Exposure Bake), and is developed to form the photoresist pattern. As the developing solution for the developing process, an alkali aqueous solution including an alkali compound such as sodium hydroxide, potassium hydroxide, sodium carbonate, tetramethylammonium hydroxide (TMAH) of the concentration of 0.1 to 10 weight % can be used. If necessary, the developing solution may further include water-soluble organic solvent such as methanol, ethanol and a surfactant of a proper amount.

Hereinafter, the preferable examples are provided for better understanding of the present invention. However, the present invention is not limited to the following examples.

EXAMPLES 1-1 TO 1-6

Synthesis of Intermediate Represented by Formula 4

Hydroxy ketone compound of Formula 2 and compound of Formula 3 having two alcohol groups or thio alcohol groups as shown in following Table 1 were added to a reactor, and then 100 ml of tetrahydrofuran (THF) of solvent was added to the reactor to dissolve the reactants. Then the dissolved reactant was stirred while maintaining at room temperature. 3.4 g of p-toluene sulfonyl acid (PTSA) was dropped to the stirred reactant. After completing the dropping of PTSA, the temperature of the reactor was regulated at 60° C. and the contents in the reactor was stirred for 12 hours. After completing the stirring, 200 ml of de-ionized water was poured to the reactor. Then the reaction product was extracted with 300 ml of dimethylchloride three times. The organic solution obtained from the above reaction was dried with anhydrous magnesium sulfate and distilled under the reduced pressure. The compound obtained by the distillation was re-crystallized with acetone to prepare target compounds (Formula 4a to 4f with yield as shown in following Table 1.

TABLE 1

| | Formula 2 | Amount used | Formula 3 | Amount used | Synthetic product | Amount synthesized | Yield |
|---|---|---|---|---|---|---|---|
| Example 1-1 | Formula 2a | 22.8 g (0.2 mol) | Formula 3a | 12.4 g (0.2 mol) | Formula 4a | 27.2 g | 86% |
| Example 1-2 | Formula 2b | 20.0 g (0.2 mol) | Formula 3a | 12.4 g (0.2 mol) | Formula 4b | 26.0 g | 90% |
| Example 1-3 | Formula 2c | 30.8 g (0.2 mol) | Formula 3a | 12.4 g (0.2 mol) | Formula 4c | 33.3 g | 84% |
| Example 1-4 | Formula 2d | 22.8 g (0.2 mol) | Formula 3a | 12.4 g (0.2 mol) | Formula 4d | 27.8 g | 88% |
| Example 1-5 | Formula 2a | 22.8 g (0.2 mol) | Formula 3b | 15.2 g (0.2 mol) | Formula 4e | 31.7 g | 92% |
| Example 1-6 | Formula 2a | 22.8 g (0.2 mol) | Formula 3c | 18.8 g (0.2 mol) | Formula 4f | 28.9 g | 76% |

EXAMPLES 2-1 TO 2-9

Preparation of Acid-Amplifier Represented by Formula 1

An intermediate of Formula 4 obtained in each of Examples 1-1 to 1-6 as shown in following Table 2 and 21.2 g (0.21 mol) of tri-ethylamine were added to a reactor, and then 100 ml of THF as the solvent was further added to the reactor to dissolve the reactants. Then the dissolved reactant was stirred while maintaining at 0° C. Here, solution which was made by dissolving sulfonyl hydride represented by Formula 5 shown in following Table 2 in 500 ml of THF, was slowly dropped with a dropping funnel to the reactor. After the dropping the sulfonyl hydride, the contents in the reactor was stirred for 6 hours while temperature of the reactor was regulated to room temperature. After the stirring, the reaction solution stirred was filtered to remove salts produced therefrom and 200 ml of de-ionized water was poured to the reactor. Then the reaction product was extracted with 300 ml of dimethylchloride three times. The organic solution obtained from the above reaction was dried with anhydrous magnesium sulfate and distilled under the reduced pressure. The compound obtained by the distillation was re-crystallized with hexane to prepare target compounds (Formula 1a to 1i) with yield as shown in following Table 2.

TABLE 2

| | Formula 3 | Amount used | Formula 5 | Amount used | Synthetic product | Amount synthesized | Yield |
|---|---|---|---|---|---|---|---|
| Example 2-1 | Formula 4a | 15..8 g (0.1 mol) | Formula 5a | 12.0 g (0.105 mol) | Formula 1a | 18.6 g | 75% |
| Example 2-2 | Formula 4b | 14.4 g (0.1 mol) | Formula 5a | 12.0 g (0.105 mol) | Formula 1b | 18.9 g | 81% |

TABLE 2-continued

| | Formula 3 | Amount used | Formula 5 | Amount used | Synthetic product | Amount synthesized | Yield |
|---|---|---|---|---|---|---|---|
| Example 2-3 | Formula 4c | 19.8 g (0.1 mol) | Formula 5a | 12.0 g (0.105 mol) | Formula 1c | 22.1 g | 76% |
| Example 2-4 | Formula 4d | 15.8 g (0.1 mol) | Formula 5a | 12.0 g (0.105 mol) | Formula 1d | 19.6 g | 79% |
| Example 2-5 | Formula 4e | 17.2 g (0.1 mol) | Formula 5a | 12.0 g (0.105 mol) | Formula 1e | 20.8 g | 79% |
| Example 2-6 | Formula 4f | 19.0 g (0.1 mol) | Formula 5a | 12.0 g (0.105 mol) | Formula 1f | 23.4 g | 83% |
| Example 2-7 | Formula 4a | 15.8 g (0.1 mol) | Formula 5b | 20.0 g (0.105 mol) | Formula 1g | 31.6 g | 92% |
| Example 2-8 | Formula 4a | 15.8 g (0.1 mol) | Formula 5c | 15.0 g (0.105 mol) | Formula 1h | 23.9 g | 86% |
| Example 2-9 | Formula 4a | 15.8 g (0.1 mol) | Formula 5d | 17.7 g (0.105 mol) | Formula 1i | 21.6 g | 71% |

$^1$H-NMR data of the compounds obtained at these examples are as follows.

$^1$H-NMR(CDCl$_3$, internal standard) of the compound represented by Formula 1a: δ(ppm) 4.52(CH, 1H), 3.78(CH$_2$, 4H), 2.91(CH$_3$, 3H), 1.73(CH$_2$, 2H), 1.56(CH$_2$, 2H), 1.45(CH$_2$, 2H), 1.36(CH$_2$, 2H).

$^1$H-NMR(CDCl$_3$, internal standard) of the compound represented by Formula 1b: δ(ppm) 4.53(CH, 1H), 3.77(CH$_2$, 4H), 2.89(CH$_3$, 3H), 1.73(CH$_2$, 2H), 1.66(CH$_2$, 2H), 1.49(CH$_2$, 2H).

$^1$H-NMR(CDCl$_3$, internal standard) of the compound represented by Formula 1c: δ(ppm) 4.33(CH, 1H), 3.78(CH$_2$, 4H), 2.91(CH$_3$, 3H), 2.01(CH, 1H), 1.56(CH$_2$, 2H), 1.47(CH, 1H), 1.39(CH$_2$, 2H), 1.09(CH$_3$, 6H).

$^1$H-NMR(CDCl$_3$, internal standard) of the compound represented by Formula 1d: δ(ppm) 4.41(CH, 1H), 3.77(CH$_2$, 4H), 2.90(CH$_3$, 3H), 1.86(CH$_2$, 2H), 1.73(CH$_2$, 2H), 1.56(CH$_2$, 2H), 1.45(CH$_2$, 2H).

$^1$H-NMR(CDCl$_3$, internal standard) of the compound represented by Formula 1e: δ(ppm) 4.50(CH, 1H), 4.01(CH$_2$, 1H), 3.86(CH$_2$, 2H), 2.91(CH$_3$, 3H), 1.72(CH$_2$, 2H), 1.56(CH$_2$, 2H), 1.45(CH$_2$, 2H), 1.36(CH$_2$, 2H), 1.12(CH$_3$, 3H).

$^1$H-NMR(CDCl$_3$, internal standard) of the compound represented by Formula 1f: δ(ppm) 4.53(CH, 1H), 2.91(CH$_2$, 4H), 2.88(CH$_3$, 3H), 2.25(CH$_2$, 2H), 1.65(CH$_2$, 2H), 1.40(CH$_2$, 2H), 1.32(CH$_2$, 2H).

$^1$H-NMR(CDCl$_3$, internal standard) of the compound represented by Formula 1g: δ(ppm) 7.82(CH, 2H), 7.31(CH, 2H), 4.46(CH, 1H), 3.77(CH$_2$, 4H), 2.44(CH$_3$, 3H), 1.75(CH$_2$, 2H), 1.56(CH$_2$, 2H), 1.46(CH$_2$, 2H), 1.35(CH$_2$, 2H).

$^1$H-NMR(CDCl$_3$, internal standard) of the compound represented by Formula 1h: δ(ppm) 4.51(CH, 1H), 3.79(CH$_2$, 4H), 3.24(CH$_2$, 2H), 1.83(CH$_2$, 2H), 1.72(CH$_2$, 2H), 1.56(CH$_2$, 2H), 1.45(CH$_2$, 2H), 1.36(CH$_2$, 2H), 0.90(CH$_3$, 3H).

$^1$H-NMR(CDCl$_3$, internal standard) of the compound represented by Formula 1i: δ(ppm) 4.64(CH, 1H), 3.80(CH$_2$, 4H), 1.74(CH$_2$, 2H), 1.52(CH$_2$, 2H), 1.44(CH$_2$, 2H), 1.35(CH$_2$, 2H).

$^1$H-NMR(CDCl$_3$, internal standard) of the compound represented by Formula 4a: δ(ppm) 4.01(CH$_2$, 4H), 3.78(CH, 1H), 1.65(CH$_2$, 2H), 1.52(CH$_2$, 2H), 1.43(CH$_2$, 2H), 1.34(CH$_2$, 2H).

$^1$H-NMR(CDCl$_3$, internal standard) of the compound represented by Formula 4b: δ(ppm) 3.99(CH$_2$, 4H), 3.80(CH, 1H), 1.75(CH$_2$, 2H), 1.66(CH$_2$, 2H), 1.55(CH$_2$, 2H).

$^1$H-NMR(CDCl$_3$, internal standard) of the compound represented by Formula 4c: δ(ppm) 4.01(CH$_2$, 4H), 3.71(CH, 1H), 2.01(CH, 1H), 1.54(CH$_2$, 2H), 1.44(CH, 1H), 1.35(CH$_2$, 2H), 1.08(CH$_3$, 6H).

$^1$H-NMR(CDCl$_3$, internal standard) of the compound represented by Formula 4d: δ(ppm) 4.00(CH$_2$, 4H), 3.15(CH, 1H), 1.88(CH$_2$, 2H), 1.62(CH$_2$, 2H), 1.54(CH$_2$, 2H), 1.48(CH$_2$, 2H).

$^1$H-NMR(CDCl$_3$, internal standard) of the compound represented by Formula 4e: δ(ppm) 4.11(CH, 1H), 3.95(CH$_2$, 2H), 3.80(CH, 1H), 1.64(CH$_2$, 2H), 1.53(CH$_2$, 2H), 1.44(CH$_2$, 2H), 1.34(CH$_2$, 2H), 1.18(CH$_3$, 6H).

$^1$H-NMR(CDCl$_3$, internal standard) of the compound represented by Formula 4f: δ(ppm) 3.65(CH, 1H), 2.91(CH$_2$, 4H), 2.25(CH$_2$, 2H), 1.65(CH$_3$, 2H), 1.39(CH$_2$, 2H), 1.34(CH$_2$, 2H).

EXAMPLES 3-1 TO 3-9 AND COMPARATIVE EXAMPLE 1

Preparation of Photoresist Composition and Formation of Photoresist Pattern Using the Photoresist Composition The acid-amplifier compound prepared in each of Examples 2-1 to 2-9 as shown in following Table 3, 2.0 g of a photo-sensitive polymer represented by Formula 6 (weight-average molecular weight (Mw): 8,500, PD(polydispersity)= 1.81), 0.08 g of triphenyl sulfonium triflate, 0.02 g of triethanolamine and 0.01 g of R08 (fat-soluble surfactant manufactured by Dainippon Ink & Chemicals (DIC), INC.) were mixed in 20 g of PGMEA as an organic solvent. Then filtering was performed to prepare the photoresist composition in each of Examples 3-1 to 3-9. Also, photoresist composition in Comparative Example 1 was prepared by using same elements in the Examples 3-1 to 3-9 except for the acid-amplifier compound.

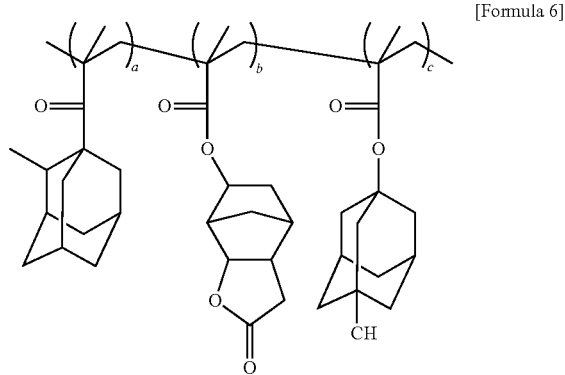

[Formula 6]

In Formula 6, a, b and c are molar ratio of respective repeating unit and 40%, 35% and 25%, respectively.

The respective photoresist composition of Examples 3-1 to 3-9 and Comparative Example 1 were applied on a wafer to form photoresist layer. The photoresist layer was pre-baked at 130° C. for 90 seconds and then was exposed to ArF excimer laser with 0.60 of numerical aperture. Next, PEB (Post Exposure Baking) was performed at 130° C. for 90 seconds. After the PEB, the photoresist layer was developed for 30 seconds to form 0.14 μm of line-and-space pattern (1:1). In the developing process, 2.38 weight % of tetramethylammonium hydroxide (TMAH) was used as the developing solution. The minimum resolution, focus margin (depth of focus), optimum level of exposure energy (sensitivity EOP) and LER (line edge roughness) of the pattern formed were measured and the results are shown in following Table 3, FIG. 1 and FIG. 2. The optimum level of exposure energy (sensitivity EOP) means the exposure amount when the pattern formed is 0.14 μm of line-and-space pattern (1:1). The depth of focus margin is defined as the depth of the resist pattern to which exposure light is reached, wherein the size of the resist pattern is 0.14 μm ±10%.

TABLE 3

| Example | Acid-amplifier compound | Amount used (g) | Minimum resolution [μm] | Focus depth [μm] | EOP [mJ/cm$^2$] | LER [nm] |
| --- | --- | --- | --- | --- | --- | --- |
| Example 3-1 | Formula 1a | 0.024 | 0.060 | 0.45 | 21 | 4.2 |
| Example 3-2 | Formula 1b | 0.022 | 0.065 | 0.40 | 22 | 4.0 |
| Example 3-3 | Formula 1c | 0.028 | 0.060 | 0.35 | 22 | 4.1 |
| Example 3-4 | Formula 1d | 0.024 | 0.065 | 0.50 | 25 | 4.2 |
| Example 3-5 | Formula 1e | 0.025 | 0.065 | 0.45 | 21 | 3.8 |
| Example 3-6 | Formula 1f | 0.027 | 0.060 | 0.40 | 24 | 5.4 |
| Example 3-7 | Formula 1g | 0.033 | 0.065 | 0.40 | 26 | 4.1 |
| Example 3-8 | Formula 1h | 0.026 | 0.060 | 0.45 | 22 | 5.0 |
| Example 3-9 | Formula 1i | 0.029 | 0.060 | 0.40 | 19 | 5.4 |
| Comparative Example 1 | — | — | 0.065 | 0.35 | 29 | 7.8 |

From Table 3, the photoresist composition including acid-amplifier compound according to the present invention further improves the LER, process speed in the photolithography and focus margin in comparison with the photoresist composition without acid-amplifier compound. Also, 50 nm line-and-space pattern can be successfully formed by using photoresist composition prepared in Examples 3-1 to 3-9 and EUV exposure instrument.

As described above, the acid-amplifier and the photoresist composition according to the present invention improves a focus margin of process as well as the LER of the photoresist pattern and the photoresist energy sensitivity, thereby forming a fine photoresist pattern.

The invention claimed is:

1. An acid-amplifier having a structure of following Formula 1,

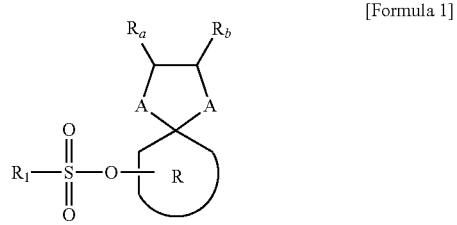

[Formula 1]

wherein in Formula 1, R is $C_4$-$C_{20}$ mono-cyclic or multi-cyclic saturated hydrocarbon, $R_1$ is $C_1$-$C_{10}$ linear hydrocarbon, $C_1$-$C_{10}$ perfluoro compound or $C_5$-$C_{20}$ aromatic compound, $R_a$ and $R_b$ are independently hydrogen atom or $C_1$-$C_4$ saturated hydrocarbon and A is independently oxygen atom (O) or sulfur atom (S);

and said acid-amplifier producing a second acid which is induced from an acid generated at an exposure to light.

2. The acid-amplifier of claim 1, wherein the linear hydrocarbon used as $R_1$ is selected from a group consisting of methyl group, ethyl group, propyl group, isopropyl group, tert-butyl group, n-butyl group and hexyl group, the perfluoro compound used as $R_1$ is selected from a group consisting of perfluoromethyl group, perfluoroethyl group, perfluoropropyl group, perfluorobutyl group and perfluorohexyl group and the aromatic compound used as $R_1$ is selected from a group consisting of benzene group, toluene group and tert-butyl benzene group.

3. The acid-amplifier of claim 1, wherein said acid-amplifier is selected from a group consisting of

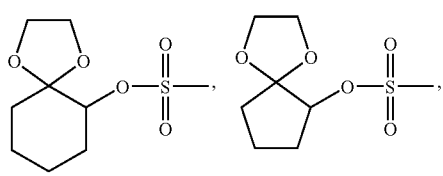

-continued

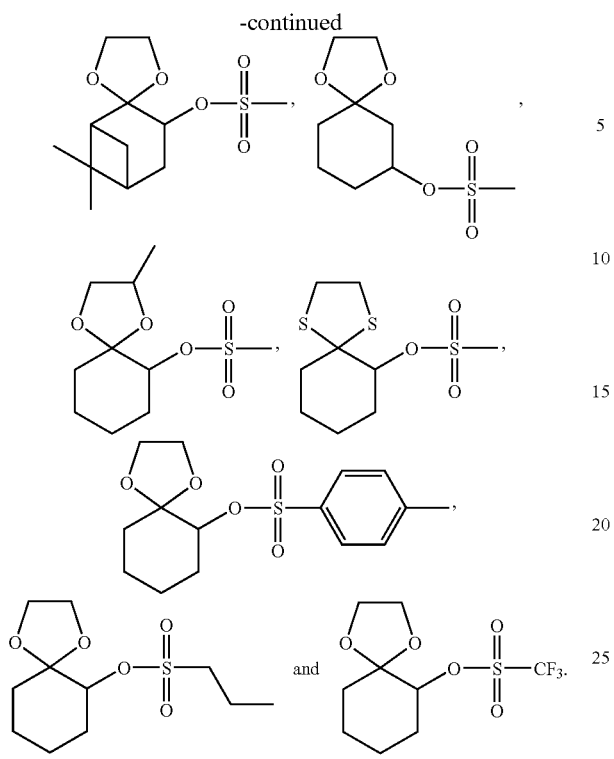

4. A photoresist composition comprising:
0.01-5.0 weight % of an acid-amplifier having a structure of following Formula 1;

[Formula 1]

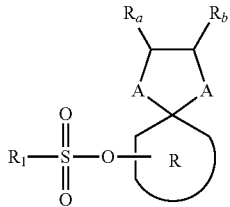

wherein in Formula 1, R is $C_4$-$C_{20}$ mono-cyclic or multi-cyclic saturated hydrocarbon, $R_1$ is $C_1$-$C_{20}$ linear hydrocarbon, $C_1$-$C_{10}$ perfluoro compound, or $C_5$-$C_{20}$ aromatic compound, $R_a$ and $R_b$ are independently hydrogen atom or $C_1$-$C_4$ saturated hydrocarbon and A is independently oxygen atom (O) or sulfur atom (S);
3-10 weight % of a photo-sensitive polymer;
0.05-10 weight part of a photo-acid generator with respect to 100 weight part of the photo-sensitive polymer; and
an organic solvent.

5. The photoresist composition of claim 4, further comprising 0.01-10 weight % of a base compound, wherein the base compound is selected from a group of consisting of tri-ethylamine, tri-iso-butylamine, tri-iso-octylamine, diethanolamine, tri-ethanolamine and mixture thereof.

6. A method for forming a photoresist pattern, comprising the steps of:
a) coating a photoresist composition on a substrate to form a photoresist layer;
wherein the photoresist composition comprises 0.01-5.0 weight % of an acid-amplifier having a structure of following Formula 1, wherein

[Formula 1]

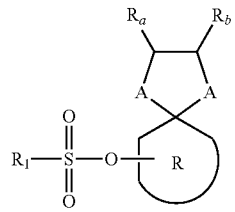

in Formula 1, R is $C_4$-$C_{20}$ mono-cyclic or multi-cyclic saturated hydrocarbon, $R_1$ is $C_1$-$C_{20}$ linear hydrocarbon, $C_1$-$C_{10}$ perfluoro compound or $C_5$-$C_{20}$ aromatic compound, $R_a$ and $R_b$ are independently hydrogen atom or $C_1$-$C_4$ saturated hydrocarbon and A is independently oxygen atom (O) or sulfur atom (S);
3-10 weight % of a photo-sensitive polymer;
0.05-10 weight part of a photo-acid generator with the respect to 100 weight part of the photo-sensitive polymer; and
an organic solvent;
b) exposing the photoresist layer to a light;
c) heating the exposed photoresist layer; and
d) developing the heated photoresist layer to form the photoresist pattern.

* * * * *